United States Patent [19]
Bornzin

[11] Patent Number: 5,697,956
[45] Date of Patent: Dec. 16, 1997

[54] IMPLANTABLE STIMULATION DEVICE HAVING MEANS FOR OPTIMIZING CURRENT DRAIN

[75] Inventor: Gene A. Bornzin, Camarillo, Calif.

[73] Assignee: Pacesetter, Inc., Sylmar, Calif.

[21] Appl. No.: 458,540

[22] Filed: Jun. 2, 1995

[51] Int. Cl.$^6$ .................................................. N61W 1/37
[52] U.S. Cl. ................................................................ 607/28
[58] Field of Search ................................... 607/9, 11, 27, 607/28, 29

[56] References Cited

U.S. PATENT DOCUMENTS

| | | | |
|---|---|---|---|
| 4,590,941 | 5/1986 | Saulson et al. | 128/419 PG |
| 4,674,508 | 6/1987 | DeCote | 128/419 PT |
| 4,726,380 | 2/1988 | Vollmann et al. | 128/419 PG |
| 4,729,376 | 3/1988 | DeCote, Jr. | 128/419 PT |
| 4,791,936 | 12/1988 | Snell et al. | 128/697 |
| 4,809,697 | 3/1989 | Causey et al. | 128/419 PT |
| 4,817,605 | 4/1989 | Sholder | 607/28 |
| 4,940,052 | 7/1990 | Mann et al. | 128/419 PG |
| 4,944,299 | 7/1990 | Silvian | 128/419 PG |
| 5,076,272 | 12/1991 | Ferek-Petric | 607/28 |
| 5,097,832 | 3/1992 | Buchanan | 128/419 PG |
| 5,176,138 | 1/1993 | Thacker | 128/419 PG |
| 5,320,643 | 6/1994 | Roline et al. | 607/28 |
| 5,447,525 | 9/1995 | Powell et al. | 607/28 |

OTHER PUBLICATIONS

Silverman, Russell M.D., et al., "Strength–Duration Pacing Threshold Test: Improved Follow–Up Efficiency & Enhanced Pacemaker Longevity," *Pace*, vol. 18, Abstract 276, (Apr. 1995, Part II).

Stokes, Kenneth B., et al., "The Electrode–Biointerface: Stimulation," *Modern Cardiac Pacing*, Chapter 3, pp. 33–77 Edited by S. Serge Barold M.D. (Futura Publishing Co., Mt. Kisco, New York (1985).

*Primary Examiner*—William E. Kamm

[57] ABSTRACT

An implantable pacemaker maintains a prescribed relationship between stimulation pulse amplitude and pulse width so as to provide an adequate safety factor above a stimulation threshold, while minimizing the current drain on the pacemaker battery. A series of stimulation pulse energies, each realized with a prescribed pulse amplitude and pulse width pair, are determined that may be used by the pacemaker as operating points. These operating points are numbered in order of increasing energy, and all adjustments of the pacing energy are made by selecting one of these operating points.

33 Claims, 7 Drawing Sheets

- - - STIMULATION VOLTAGE (VOLTS)
—— STIMULATION THRESHOLD (VOLTS)

IMPLANTABLE STIMULATION DEVICE HAVING MEANS FOR OPTIMIZING CURRENT DRAIN

FIELD OF THE INVENTION

The present invention relates to implantable medical devices and methods, and more particularly to an implantable pacemaker or pacemaker system that maintains a prescribed relationship between the amplitude and pulse width of a stimulation pulse so as to assure the stimulation pulse achieves capture while minimizing the current drain on the pacemaker battery.

BACKGROUND OF THE INVENTION

A pacemaker is an implantable medical device that selectively generates and delivers electrical stimuli to muscle tissue of the heart at a controlled rhythm or rate for the purpose of forcing such muscle tissue to depolarize, and hence contract, thereby maintaining a heart rhythm or rate designed to optimally pump blood through a patient's body.

A pacemaker includes a battery that provides the electrical power for operating the pacemaker circuits, as well as for generating the stimulation pulses that are delivered to the heart. Most of the bulk and weight associated with an implanted pacemaker results from such battery. Further, the vast majority of the energy stored in the pacemaker battery is spent through generation and delivery of the electrical stimulation pulses, with only a small fraction of such energy being spent to power the pacemaker circuits. Hence, in order to extend the life of the battery as long as possible, it is important to design and operate the pacemaker so that the stimulation pulses are generated only when needed, and when needed only consume a minimal amount of the battery's stored energy.

A given stimulation pulse depolarizes cardiac muscle tissue only if its energy is above a stimulation threshold. If so—if the energy of the stimulation pulse is above the stimulation threshold—the stimulation pulse is said to "capture" the heart. If not—if the energy of the stimulation pulse is below the threshold—the stimulation pulse does not achieve capture, and the energy spent in the stimulation pulse is wasted. Thus, a first criteria for the efficient use of the energy stored in the pacemaker battery is to assure that the energy of every needed stimulation pulse is above the stimulation threshold, thereby effectuating capture.

Stimulation thresholds, although related to the power contained within the stimulation pulse, are typically expressed in terms of voltage or current, depending on which parameter (voltage or current) is easier to measure. For example, in constant current systems, current is typically easier to measure. In constant voltage systems, voltage is typically used. Since the present invention can be utilized in either a constant current system or a constant voltage system, hereafter, the threshold at which capture occurs will be referred to as the "stimulation threshold", and the stimulation pulse (whether expressed as voltage or current) will be referred to as the "stimulation pulse amplitude".

It is well known that the stimulation threshold of the heart is not fixed but varies under a variety of conditions. Sleeping and eating cause about a 20% increase in stimulation threshold. Posture and exercise change the stimulation threshold about 15 to 20%. During the lead maturation process, stimulation thresholds typically increase to a peak during the first three months, then stabilize to a lower level. Drugs also have a profound effect on stimulation thresholds. Thus, in setting the energy (amplitude and/or pulse width) of the stimulation pulse, there is a need to account for such variations in the stimulation threshold so that capture will still occur despite such variations.

Typically, the stimulation threshold is measured by fixing the pulse width and varying the amplitude of the pulse. Once the stimulation threshold is established, the pacemaker is programmed to generate a stimulation pulse that is in excess of the measured stimulation threshold by a prescribed safety factor, commonly referred to in the art as the "safety margin". The purpose of the safety factor is to prevent capture from being lost due to stimulation threshold variation. Typically, a safety factor of 1.7 to 2 is selected, meaning that the stimulation pulse amplitude is set to a value that is 1.7 to 2 times greater than the measured stimulation threshold.

As is known in the art, a more systematic way to consider stimulation threshold is to view it as a continuous function described by the strength-duration relationship. See, e.g., Stokes and Bornzin, "The Electrode-Biointerface: Stimulation", Chapter 3 of Modern Cardiac Pacing, edited by S. Serge Barold, MD (Futura Publishing Co., Mt. Kisco, N.Y. 1985). The essence of the strength-duration relationship is that for very narrow pulse widths, a large stimulation pulse amplitude is required to effectuate capture, and for wide pulse widths, a lower stimulation pulse amplitude is required to effectuate capture. What this means, as described more fully below, is that there are a variety of stimulation pulse amplitudes and pulse widths that may be used to effectuate capture, and a corresponding variety of stimulation pulse amplitudes and pulse widths that can be programmed for use by a pacemaker to effectuate capture with an adequate safety factor.

Heretofore, it has been common practice when programming a pacemaker to arbitrarily select the pulse width, and then set the stimulation pulse amplitude at, for example, two times the threshold voltage at that pulse width, thereby providing a suitable safety factor (e.g., a safety factor of two) without any consideration whatsoever as to how much current drain the amplitude/pulse width setting may have on the pacemaker's battery. What is needed, however, is a pacemaker, or pacing system, wherein the stimulation pulse amplitude and width can not only be set to a value that assures capture with an adequate safety factor, but that also provides a minimum current drain on the pacemaker battery.

SUMMARY OF THE INVENTION

The present invention addresses the above and other needs by providing an implantable pacemaker capable of generating electrical stimulation pulses of varying (e.g., programmable) energies, wherein each electrical stimulation pulse thus generated is formed using an optimal pulse width and pulse amplitude combination that produces minimal current drain on the pacemaker battery, and yet still achieves capture with an adequate safety factor.

In accordance with one aspect of the present invention, the pulse width and pulse amplitude of the stimulation pulse generated by the pacemaker are not independently selectable or programmable. Rather, each stimulation pulse is formed by an optimal combination of a specific pulse width and a specific pulse amplitude, with a series of such optimally-combined pulse amplitude/pulse widths, each having a different energy, being made available to the pacemaker as possible operating points.

One embodiment of the invention may be characterized as an implantable pacemaker that includes: (a) a battery; (b)

pulse generating means for selectively generating electrical stimulation pulses at appropriate times for the purpose of depolarizing cardiac tissue, where the electrical stimulation pulses are formed from electrical energy derived from the battery; and (c) pulse setting means for making the pulse width and amplitude of the electrical stimulation pulses assume a pulse amplitude/pulse width combination that achieves capture with a selected safety factor, and that minimizes the energy drain on the battery. Such pacemaker preferably includes a memory circuit wherein an energy data word is stored. The energy data word defines the energy of the stimulation pulse, and includes a pulse amplitude portion and a pulse width portion. The pulse amplitude portion and the pulse width portion are thus always used together, so that pulse amplitude and pulse width are not independent variables. This is done so that both the pulse amplitude and the pulse width of the stimulation pulse may be assigned values that together provide the selected safety factor while minimizing the energy drain on the battery.

Another embodiment of the invention may be characterized as a pacing system that includes both an implantable pacemaker and an external programmer. The pacing system performs, inter alia, the function of stimulating cardiac tissue with electrical stimulation pulses, where the stimulation pulses are formed to have a specific pulse amplitude and a specific pulse width. When delivered to the cardiac tissue, the energy of the stimulation pulse resulting from the specific pulse amplitude and pulse width is above a stimulation threshold by a prescribed safety factor. The implantable pacemaker used in such pacing system includes: (a) a battery, (b) control means, powered by the battery, for determining stimulation threshold, and (c) stimulation means, controlled by the control means, for generating electrical stimulation pulses of a prescribed pulse width and amplitude, and for delivering the electrical stimulation pulses to the cardiac tissue at appropriate times with the stimulation pulses being generated from electrical energy stored in the battery. The external programmer used in such pacing system includes: (a) means for selectively establishing a communication link with the implantable pacemaker, and (b) means for defining, through the communication link, the prescribed pulse amplitude and width of the stimulation pulses to be generated by the stimulation means of the implantable pacemaker. Significantly, the prescribed pulse amplitude and width of each stimulation pulse comprises a pulse amplitude/width combination that maintains a prescribed safety factor while drawing minimal energy from the battery of the implantable pacemaker.

Further, the invention may be characterized as a method automatically determining an optimal combination of stimulation pulse width and stimulation pulse amplitudes so that the pacemaker current drain is minimized while maximizing the safety factor of the pacemaker. Such method includes: (a) determining a stimulation threshold for a particular patient as a function of stimulation pulse width; (b) determining a stimulation pulse amplitude as a function of stimulation pulse width so as to achieve a given safety factor above the stimulation threshold; (c) computing a pacing current drain as a function of the stimulation pulse widths and amplitudes determined in step (b); (d) selecting an optimal stimulation pulse amplitude and pulse width combination that provides a minimal pacing current drain as a function of pacing energy; and (e) automatically programming the pacemaker to the optimal pacing energy using the stimulation pulse amplitude and pulse width combination determined in step (d).

In a preferred application of such method, steps (c) and (d) are carried out by first defining the relationship between pacing drain current, pulse width, pulse amplitude and safety factor as a function of stimulation threshold. Then, selecting a first stimulation threshold, corresponding to a first strength-duration curve, and generating a first data set that relates the pacing drain current, pulse width, and pulse amplitude at the first stimulation threshold. Next, additional stimulation thresholds, corresponding to additional strength-duration curves, are selected and respective additional data sets are generated that relate the pacing drain current, pulse width, pulse amplitude and safety factor at each of the additional stimulation thresholds. In this manner, a family of data sets is obtained that relates pacing drain current, pulse width, pulse amplitude and safety factor at a plurality of stimulation thresholds (corresponding to a plurality of strength-duration curves). Once the family of data sets has been obtained, the information contained in the family of data sets is evaluated to determine an optimal series of pulse width and pulse amplitude pairs that may be used as operating points for the pacemaker, the optimal series being defined as the pulse amplitude/pulse width pair at each of the plurality of stimulation thresholds which has the lowest current drain. The pulse amplitude/pulse width pairs in such optimal series are then numbered or otherwise sequenced or arranged in order of increasing stimulation efficacy. The sequence may be stored in the pacemaker's memory, or downloaded from an external device. Finally, operating points for the pacemaker are selected from the numbered pulse amplitude/pulse width pairs so as to provide a selected safety factor.

In an alternate embodiment of the present invention, steps (c) and (d) are carried out by first defining the relationship between pacing drain current, pulse width, and pulse amplitude as a function of stimulation threshold. Then, measuring a patient's current stimulation threshold using at least one pulse width. Next, the method includes the step of determining a strength-duration curve, determining a plurality of pulse amplitude/pulse width combinations which will ensure capture at a desired safety factor above the strength-duration curve, and selecting an optimal pulse amplitude/pulse width combination defined as one of the plurality the pulse amplitude/pulse width pairs which both ensures capture at the desired safety factor and has the lowest current drain. Thereafter, if capture is lost, the method includes repeating the above steps at the patient's new stimulation threshold.

Thus, it is a feature of the present invention to provide an implantable pacemaker that overcomes the aforementioned shortcomings of prior art pacemakers.

More particularly, it is a feature of the present invention to provide an implantable pacemaker or pacing system that provides or defines stimulation pulses having a pulse amplitude/width combination that achieves capture with a desired safety factor, while at the same time minimizing the current drain on the pacemaker's battery.

It is an additional feature of the invention to provide an implantable pacemaker that exhibits a long battery life by minimizing the energy drawn from the battery by its stimulation pulses.

It is still a further feature of the invention to provide an implantable pacemaker that efficiently utilizes the energy stored in its battery, thereby promoting a long battery life, and hence a long pacemaker life.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 5:
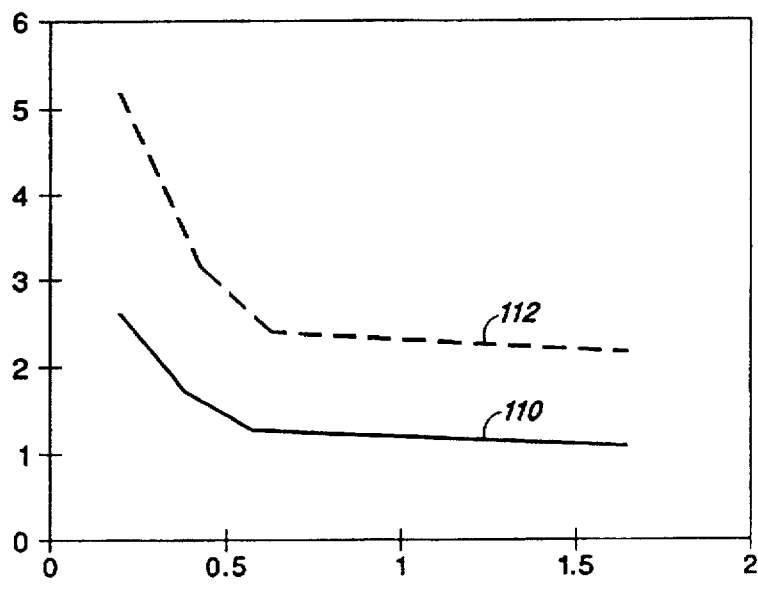
FIG. 5 is a graph that shows a representative strength-duration curve and a stimulation voltage curve at a safety factor of two.

Although the present invention will be described in terms of a constant voltage system, one of skill in the art could easily adapt the present invention into a constant current system. For example, the strength-duration curve, presented in FIG. 5, is plotted as a function of voltage on the y-axis, but one of skill in the art would be able to plot a strength-duration curve as a function of current and could further determine an optimum current amplitude as a function of pulse width.

As summarized above, the present invention relates to a pacemaker or pacing system wherein the amplitudes and widths of the electrical stimulation pulses generated by the pacemaker have been optimized to provide a maximal safety factor while maintaining a minimum current drain on the battery of the pacemaker.

To better understand and appreciate the invention, it will first be helpful to review the basic design and operation of an implantable pacemaker or pacing system.

Figure 1:
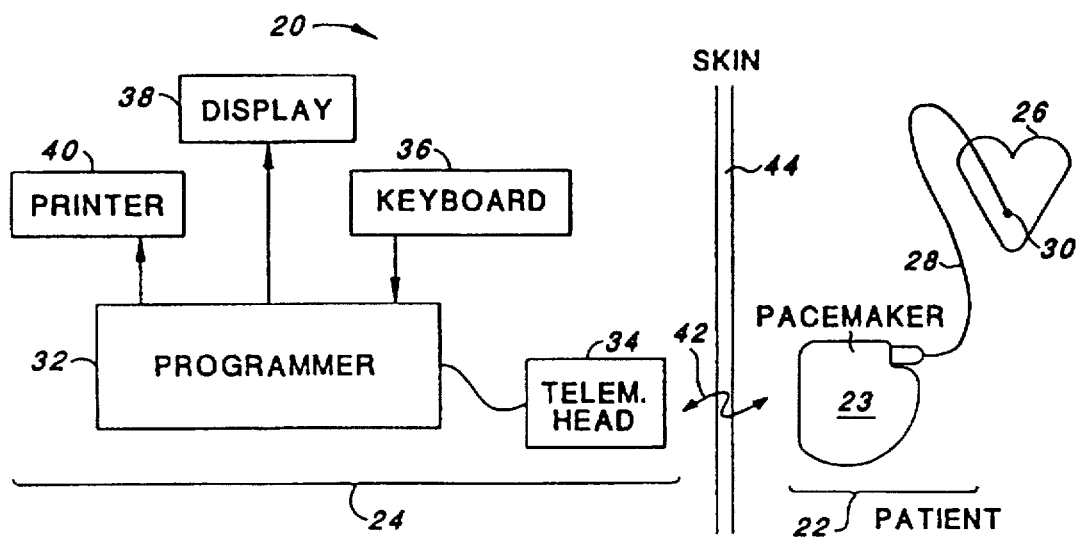
FIG. 1 is a block diagram of a pacing system made in accordance with the present invention.

Accordingly, as shown in FIG. 1, there is shown a block diagram of a pacing system 20. Such pacing system 20 includes an implantable portion 22 and an external (non-implanted) portion 24. The implanted portion 22 includes an implantable pacemaker 23. The pacemaker 23 is implanted within a patient, in conventional manner, and the pacemaker is electrically coupled to the patient's heart 26 by way of at least one pacing lead 28. The pacing lead 28 includes at least one electrode 30 through which electrical stimulation pulses are delivered to the heart, or through which cardiac activity, e.g., depolarization of the cardiac tissue, is electrically sensed. Unipolar, bipolar, or multipolar pacing/sensing electrode configurations, as are known in the art, may be used.

The external portion 24 includes a programmer 32 connected to a telemetry head 34. The programmer 32 includes a keyboard 36, or equivalent input device, for allowing a user thereof to input commands and data into the pacing system. The programmer also includes some type of display 38, and/or printer 40, to allow data and other operational parameters associated with the pacing system to be displayed. In some external programmers, the telemetry head 34, keyboard 36, display device 38 and/or printer 40 may be incorporated into an integral programming unit.

In operation, the programmer 32 is used to program the pacemaker 23. This is done by establishing a telemetry link, represented by the wavy arrow 42, between the telemetry head 34 of the programmer 32 and the pacemaker 23. When the pacemaker 23 is implanted in the patient, such telemetry link is established through the skin 44 of the patient. Once the telemetry link is established, certain command words, as selected by the user of the programmer (e.g., a physician) are telemetered from the programmer to the pacemaker through the telemetry link. Appropriate circuitry is included in the pacemaker for receiving such command words and storing them in a memory circuit of the pacemaker, described below. Such command words define the programmable operational parameters of the pacemaker, such as base pacing rate, the pacing mode, etc., as is known in the art. The pacemaker then provides stimulation pulses to the patient's heart 26 as controlled by such operational parameters.

In the prior art, two operational parameters are used to define the stimulation pulse that is generated by the pacemaker 23 for delivery to the heart 26. These two parameters are pulse amplitude and pulse width, each of which are independently programmable, thereby allowing the programming physician (or other medical personnel) to select any desired combination of pulse width and pulse amplitude for the stimulation pulse.

The present invention recognizes that being able to independently program pulse width and pulse amplitude may not necessarily provide optimal pacing, where "optimal" is a term that implies maintaining a desired or adequate safety factor while minimizing the current drain on the pacemaker battery. Hence, the present invention does not allow independent programming of pulse amplitude and pulse width, but rather allows only the programming of pulse energy, selected from a series of stimulation pulses of increasing or decreasing energy that have been formed to provide optimal pacing.

Figure 2:
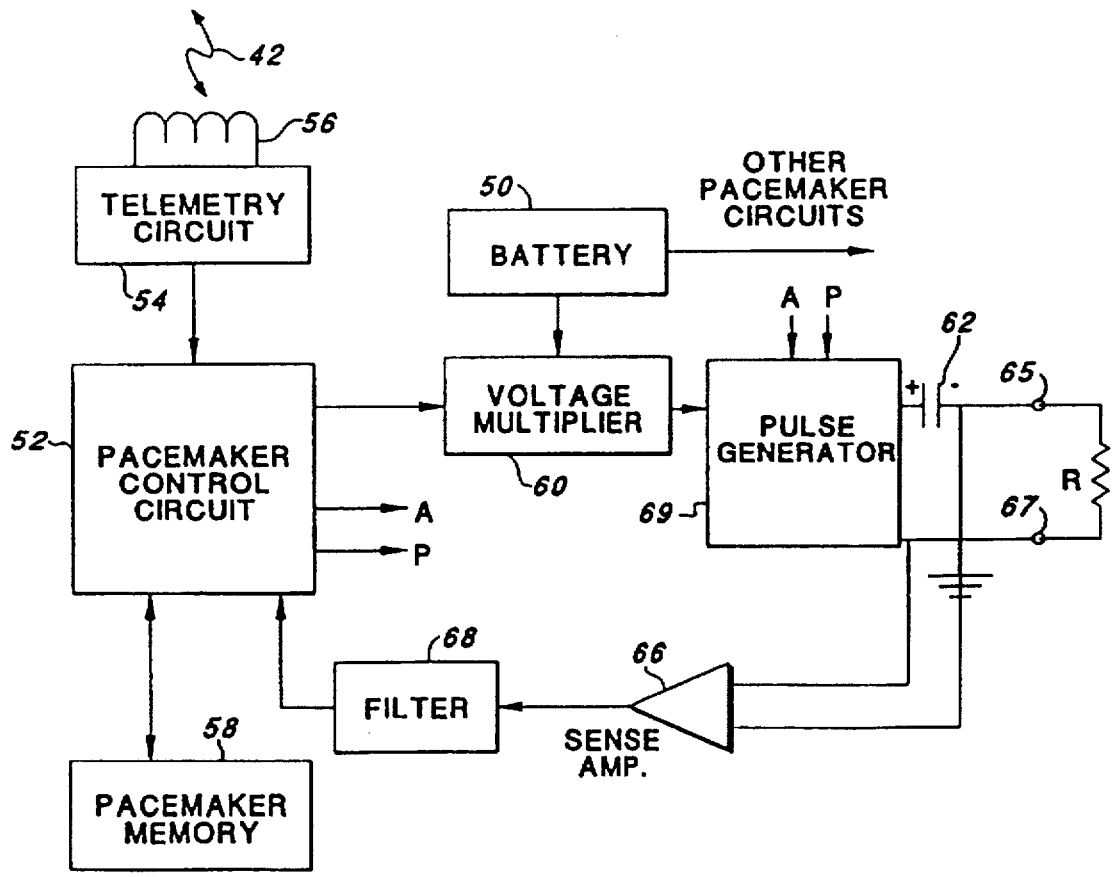
FIG. 2 is a functional block diagram of the implantable pacemaker of FIG. 1.

As shown in the pacemaker block diagram of FIG. 2, the pacemaker 23 includes a battery 50 and various electronic circuits that are powered by the battery 50. The electronic circuits include a pacemaker control circuit 52 coupled to a pacemaker memory circuit 58 and a telemetry circuit 54. The telemetry circuit 54 includes a coil 56, or other suitable antenna, and is adapted to receive or send signals through the telemetry link 42. The battery 50, in addition to powering the pacemaker circuits, is also coupled to a voltage multiplier circuit 60. The voltage multiplier circuit 60 steps up (or multiplies) the battery voltage by a selected integer (e.g., 1, 2 or 3) and charges an output capacitor 62, through a pulse generator circuit 69, using the resulting stepped-up voltage. Because the output capacitor 62 is charged through the pulse generator circuit 69 with a voltage that may be greater than the battery voltage, the voltage multiplier circuit is sometimes referred to as a "charge pump circuit", because it "pumps" the output capacitor 62, through the pulse generator circuit 69, with a charge from the battery that may be greater than the battery voltage. The capacitance of the output capacitor 62 is a value "C" that is typically 5 µF.

The output capacitor 62 is coupled to an output terminal 65, with a return through output terminal 67, through a suitable output switch (not shown) within the pulse generator circuit 69. The pulse generator circuit 69 controls the discharge of the capacitor 62 by switching the capacitor to ground, so that the charge on the capacitor is discharged through a load, represented in FIG. 2 as a resistor R. Such resistance R represents the pacing load, and the discharge represents the "stimulation pulse" that is delivered by the pacemaker 23 through the lead(s) 28 to the heart 26.

The amplitude of the stimulation pulse is controlled by the pulse generator circuit 69 which determines how much charge is stored on the output capacitor 62. The width of such stimulation pulse, for relatively short stimulation pulses (e.g., less than a few milliseconds), is controlled by how long the pulse generator circuit 69 switches the output capacitor 62 to ground. For longer stimulation pulses, the RC time constant associated with the discharge also influences the pulse width. Both the amplitude and width of the stimulation pulse are thus parameters that are controlled by the pacemaker control circuit 52. Such control is symbolically depicted in FIG. 2 through the use of two control signals: a first control signal "A" that controls the amplitude of the stimulation pulse; and a second control signal "PW" that controls the width of the stimulation pulse. The output capacitor 62 and the pulse generator circuit 69, in cooperation with the voltage multiplier circuit 60, thus comprise a pulse generator circuit 69 that generates a stimulation pulse as controlled by the pacemaker control circuit 52 having a prescribed amplitude "A" and pulse width "PW".

It is noted that while a single output capacitor 62 and output switch 64 are described to functionally represent the pulse generator circuit 69, in general the pulse generator circuit 69 may include a more complicated arrangement of components, e.g., a pulse forming network, as is known in the art.

Significantly, each stimulation pulse generated by the pulse generator circuit draws or drains a fixed amount of energy from the pacemaker battery 50. But, as discussed in more detail below, the amount of current drain on the battery produced by a given stimulation pulse varies as a function of the pulse width, amplitude, and other factors, such as the charge pump factor. To prolong battery life, it is thus imperative that stimulation pulses be generated only when needed, and when needed be formed with a particular pulse width and pulse amplitude combination that minimizes the current drain on the battery. The present invention advantageously achieves this mandate.

As shown in FIG. 2, a sense amplifier 66 is also coupled to the output terminals 65 and 67 of the pacemaker 23. Such sense amplifier senses any electrical signals that may appear on the output terminals, such as the electrical signals that occur upon the depolarization of cardiac tissue. Typically, such sense amplifier is blanked (or disabled) during the time that a stimulation pulse is being delivered through the output terminals 65 and 67 so that the large stimulation pulse does not saturate or otherwise adversely impact the performance of the sense amplifier.

Any signals sensed by the sense amplifier 66 are filtered by a filter circuit 68 (which filter may actually be part of the amplifier 66) and presented to the pacemaker control circuit 52. The depolarization of the atria of the heart, for example, is characterized by the generation of an electrical signal, present in the electrogram signal, commonly referred to as a P-wave. Similarly, the depolarization of the ventricles of the heart is characterized by a much larger electrical signal, commonly referred to as the "R-wave". It is thus the function of the sense amplifier 66, and related circuitry, to sense the occurrence of P-waves and/or R-waves, which sensed P-waves and/or R-waves are used by the pacemaker control circuit 52 as indications that the heart is contracting on its own, and that no stimulation pulse(s) are needed.

In a common mode of operation, demand pacing, the pacemaker control circuit 52 includes one or more timer circuits that define a basic pacing interval. If, during the pacing interval, a signal is sensed through the sense amplifier 66 indicating the depolarization of cardiac tissue, then no stimulation pulse is generated, and the basic pacing interval is restarted. Should the pacing interval elapse without the sensing of a depolarization, then a stimulation pulse is generated at the conclusion of the pacing interval. In this manner, then, stimulation pulses are provided on demand, e.g., only when needed, at a rate determined by the programmed pacing interval.

In modern pacemakers, the pacing interval is programmed into the pacemaker memory 58 through the telemetry link 42 from the external programmer 24 (FIG. 1), and may (in certain types of rate-responsive pacemakers) vary with a sensed physiological parameter. Other control parameters, such as the parameters that define the pacing mode, the stimulation pulse amplitude and stimulation pulse width, are similarly programmed into the pacemaker memory 58. The pacemaker control circuit 52 then looks to the pacemaker memory 58 to retrieve whatever control parameters are stored therein and controls the operation of the pacemaker accordingly. If the pacemaker needs to be reprogrammed, then the physician, using an external programmer 24 (FIG. 1), simply stores new control parameters in the pacemaker memory 58 to effectuate the desired changes in the pacemaker operation.

Those of skill in the pacing art will recognize that the above description of a pacemaker is greatly simplified. There are numerous timing intervals, control parameters, and operational modes, employed by modern pacemakers. A more detailed description of a pacemaker may be found, e.g., in U.S. Pat. Nos. 4,940,052; 4,944,299; 5,176,138; and 5,097,832; incorporated herein by reference. For purposes of the present invention, however, the above simplified description of the pacemaker 23 is sufficient because the present invention is directed primarily to the manner in which the pulse amplitude and pulse width of the stimulation pulse is defined.

Figure 3A:
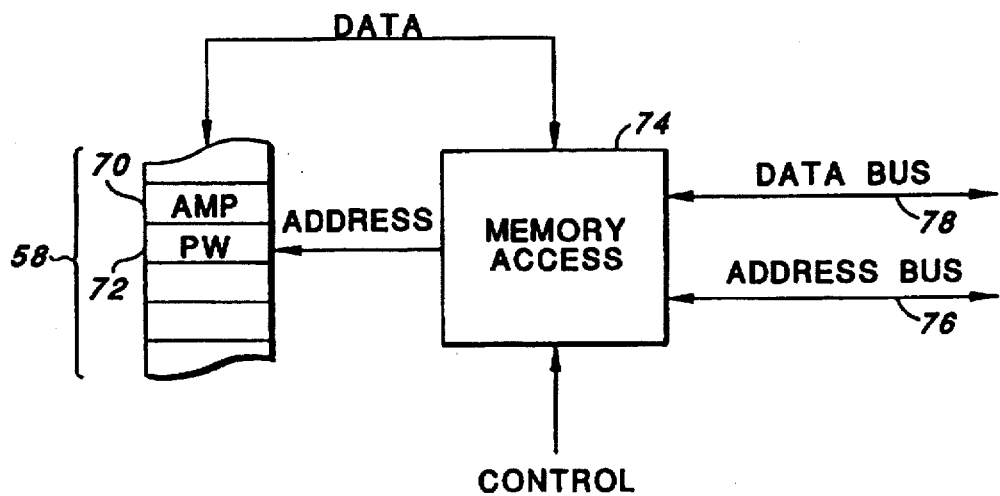
FIG. 3A is a block diagram that details one type of memory organization that may be used by the pacemaker of FIG. 2.

In FIG. 3A, a diagram is shown illustrating one way in which the pacemaker memory 58 may be configured for purposes of the present invention. As seen in FIG. 3A, the memory 58 includes a plurality of storage locations, each having a unique address. A given data word, or control parameter, is stored in a known memory location, i.e., at a known address. For example, a first memory location 70 may have an amplitude (AMP) data word stored therein; and a second memory location 72 may have a pulse width (PW) data word stored therein. Access to a given memory location is made by way of a memory access circuit 74, which may be of conventional design. Such memory access circuit 74 interfaces with a data bus 78 and an address bus 76 from the pacemaker control circuit 52. In anticipation of generating a stimulation pulse, the pacemaker control circuit generates a sequence of addresses where the amplitude and pulse width data words are stored, and places such addresses on the address bus 76. In response, the memory access circuit retrieves the data from such addressed memory locations, placing the data words thus retrieved, on the data bus 78. The data words are then transferred from the data bus 78 to appropriate registers or other logic circuits within the pacemaker control circuit 52. Thereafter, the data words are used to define an appropriate parameter, e.g., the amplitude of the stimulation pulse and/or the duration (width) of the stimulation pulse.

In accordance with the present invention, the AMP data word stored in memory location 70 and the PW data word stored in memory location 72 share a predetermined relationship, as described more fully below, and are not independent of each other. This is in contrast to prior art pacemakers where the amplitude and pulse width have typically been independent parameters that could be programmed to any desired value within a plurality of possible values. That is, in a typical prior art pacemaker, the pulse width could be set to any value between 0.2 milliseconds and 1.6 milliseconds in increments of, for example, milliseconds; while pulse amplitude could be set to any value between 0.5 volts and 7.5 volts in increments of 0.5 volts. Hence, what a physician would typically do would be to program an arbitrary pulse width (e.g., 1 msec), and then set the pulse amplitude at some acceptable value that would achieve capture with an adequate safety factor. Such setting, however, was done without regard to the impact it would have on the pacing current drain. Hence, less than optimal pacing would most often result.

In at least one prior art method (see U.S. Pat. No. 4,590,941, Saulson et al.), a pacemaker is disclosed which has paired combinations of monotonically increasing charge density (e.g., 2 mA/0.2 ms, 3 mA/0.3 ms, 4 mA/0.4 ms, etc.). However, these paired combinations of current amplitude and pulse width also did not take into account the impact of the pacemaker electronic circuitry (e.g., voltage doubling, etc.) on the overall current drain.

Thus, an important aspect of the present invention is that the AMP data word and the PW data word comprise a paired data set that takes into account both the current drain required for stimulation at a desired safety factor and the current drain required by the pacemaker electronics. Such paired data set may be defined or determined in numerous ways. One way to define such paired data set is in the programmer 32 (FIG. 1). That is, the programmer 32 is configured to provide a list of possible energies for the stimulation pulse, and the physician selects which energy is to be used. An AMP data word and a PW data word that correspond to the selected energy are then transferred to the pacemaker memory for storage therein. Such AMP data word and PW data word thus comprise a paired data set that provides optimal pacing for the pacemaker, i.e., a stimulation pulse that paces at a preselected safety factor, and that minimizes the drain current on the battery.

Another way to define the paired data set that provides optimal pacing is in the pacemaker 23. That is, the pacemaker, and more particularly the pacemaker control circuit 52 and operational control data loaded into the memory 58, generates or looks-up the appropriate paired data set of amplitude and pulse width information based on a selected pacing energy. For example, the available pacing energies may simply be identified as a sequence of pacing numbers ranging from 1 to 25. The physician simply selects a pacing number, with a 1 being the lowest possible pacing energy, and a 25 being the highest possible pacing energy, and such pacing number is transferred to the pacemaker control circuit through the telemetry link. When received at the pacemaker, the pacing number is stored and/or converted to the appropriate paired set of amplitude and pulse width data that cause an optimal stimulation pulse to be generated, when needed.

It is noted that such conversion of a "pacing number" to an optimal pulse width and pulse amplitude stimulation pulse could, of course, also be performed in the programmer, with the resulting paired data set being sent to the pacemaker for storage, as described above.

It is contemplated that in some instances, and in some models of pacemakers, there will be included in the pacemaker 23 appropriate sensors that ascertain when there is a need to adjust the pacing energy. Hence, although the pacing energy is initially programmed to a starting value (i.e., a starting pulse amplitude and width combination), it may adaptively and automatically change thereafter as a function of a sensed parameter or condition. For example, the pacemaker may include appropriate circuitry that periodically measures the stimulation pulse energy needed to effectuate capture, and then automatically increases the stimulation pulse energy above such threshold level by a predetermined safety factor. Alternatively, the pacemaker may, by sensing the heart rate, identify a tachycardia condition (a fast heart rhythm) which may call for increased stimulation energy to ensure capture. In such situations, e.g., where the pacemaker adaptively changes the pacing energy as a function of a sensed parameter or condition, the present invention makes such energy adjustments in an optimal manner. That is, each increase in pacing energy is achieved by selecting a stimulation pulse having a particular pulse width and pulse amplitude combination that provides an incremental change in the pacing energy while still minimizing pacing current drain and maintaining the prescribed safety factor.

Figure 3B:
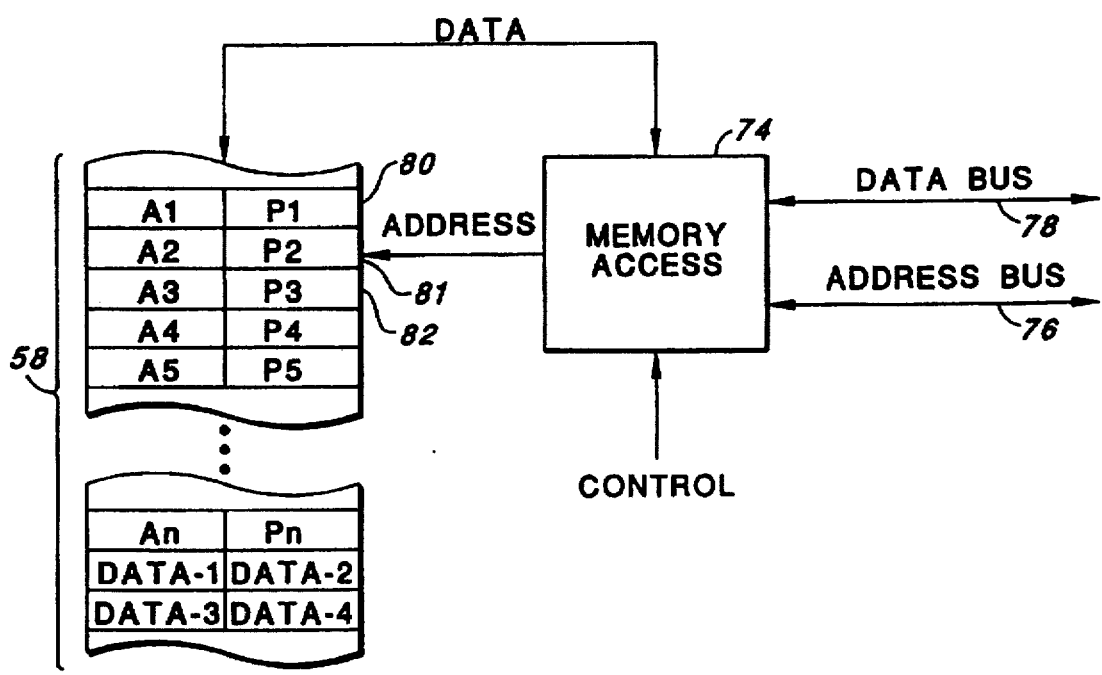
FIG. 3B is a block diagram that details another type of memory organization that may be used by the pacemaker of FIG. 2.

In FIG. 3B, one way of achieving such adaptive changes in the pacing energy in accordance with the present invention is illustrated. As shown in FIG. 3B, the pacemaker memory 58 includes a plurality of paired memory locations. A first paired memory location 80 includes an amplitude data word A1 and a pulse width data word P1; a second paired memory location 81 includes an amplitude data word A2 and a pulse width data word P2; and so on, with an nth memory location including an amplitude data word An and a pulse width data word Pn. Each paired set of data words is selected, as described below, to provide optimal pacing, yet each provides a different pacing energy. Thus, the pacemaker control circuit 52 can select one of the pacing energies (i.e., one of the paired set of data words) for a given stimulation threshold; and thereafter, based on a sensed parameter or condition, adaptively change the selected pacing energy by selecting a different paired set of data words.

In lieu of separate data words, it should be pointed out that the amplitude and pulse width paired information stored in the pacemaker memory 58 may be included in a single data word, with a first portion of the data word (e.g., a first group of bits) defining the amplitude information, and a second portion of the data word (e.g., a second group of bits) defining the pulse width information.

Figure 4:
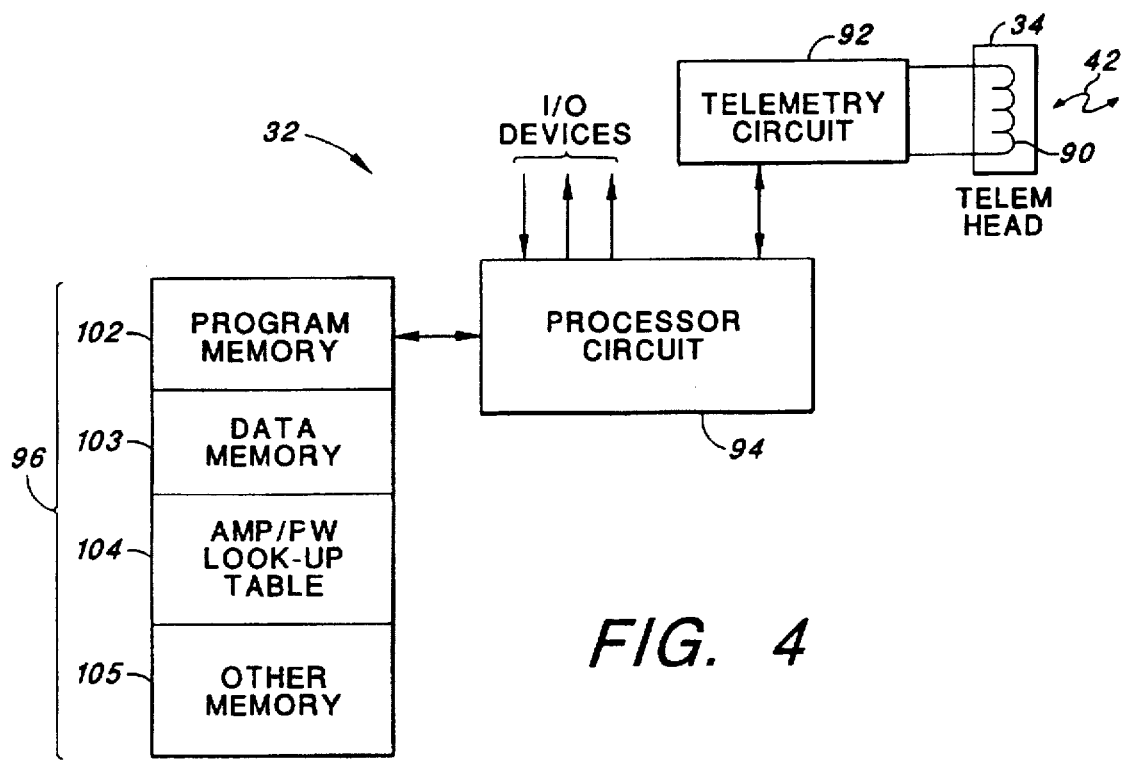
FIG. 4 is a functional block diagram of the programmer of FIG. 1.

In FIG. 4, a functional block diagram of the programmer 32 (FIG. 1) is shown. Like the block diagram of the pacemaker 23 (shown in FIG. 2), the block diagram of the programmer in FIG. 4 is greatly simplified. A more detailed description of a suitable programmer may be found, e.g., in U.S. Pat. Nos. 4,791,936 and 4,809,697; incorporated herein by reference. Even though FIG. 4 is simplified, however, it shows the main components of the programmer 32 that are used with the present invention, in combination with the input/output devices (shown in FIG. 1), and is thus adequate for purposes of understanding how to use and practice the present invention.

The programmer 32 is coupled to the telemetry head 34. The telemetry head 34 includes a suitable coil 90 or antenna that is connected to an external telemetry circuit 92, which telemetry circuit 92 comprises part of the programmer 32. The telemetry circuit 92 and the coil 90 are designed to transmit signals to and receive signals from the pacemaker telemetry circuit 54 (FIG. 2) through the telemetry link 42.

The main components of the programmer 32 include a suitable processor circuit 94 and memory circuit 96. The processor circuit 94 may be realized, e.g., using any of a number of commercially available microprocessor circuits. The memory circuit 96 is typically divided into several memory areas. For example, a memory area 102 may be dedicated to storing an operating program(s), whereas a memory area 103 may be dedicated to storing data, e.g., electrogram data, received from the pacemaker. In order to practice the present invention, a third memory area 104 may contain paired amplitude and pulse width data words, where each pair defines an operating point for the stimulation pulses generated by the pacemaker. That is, the memory area 104 may effectively contain an amplitude/pulse width look-up table, generated as described below, that identifies the pulse amplitude and pulse width combinations that are programmed into the pacemaker memory in order to maintain an adequate safety factor while minimizing pacing current drain. Other memory areas 105 may be used by the processor 94 for other purposes, not related to the present invention.

Those of skill in the art are well versed in the techniques used to operate and program the pacing system(s) shown in FIGS. 1–4. Hence, the remaining description of the invention will focus on how the optimal operating points (i.e., optimal pulse width and pulse amplitude pairs) of the pacemaker are determined, regardless of whether such optimal operating points are stored in the pacemaker as a set of operating points that can be adaptively selected by the pacemaker control circuit as a function of some sensed parameter or condition (as could be achieved using the pacemaker memory configuration shown in FIG. 3A), or whether such operating points are programmed into the pacemaker from an external programmer on an as-needed basis, one operating point at a time (as could be achieved using the pacemaker memory configuration shown in FIG. 3A).

A key factor that must be considered in practicing the invention is that pacing should always occur at an energy level that exceeds the stimulation threshold by an adequate safety factor. Otherwise, capture may not occur, and the energy included in the stimulation pulse will be wasted.

As previously mentioned, stimulation threshold is best viewed as a continuous function described as a strength-duration curve. In FIG. 5, a representative strength-duration curve is shown as the solid curve 110. FIG. 5 shows that for very narrow pulse widths, a large stimulation amplitude is required to effectuate capture; while for wider pulse widths, a lower stimulation amplitude is required to effectuate capture.

In order to achieve a desired safety factor, it is necessary that the programmed stimulation pulse amplitude be above the stimulation threshold by a prescribed amount, e.g., double the stimulation threshold. A stimulation amplitude, needed to achieve a safety factor of two, is shown in FIG. 5 as a dotted curve 112, and will be referred to as the "Iso-Safety Factor Curve". The Iso-Safety Factor Curve 112 shows that a variety of stimulation pulse widths and amplitudes can achieve a safety factor of two.

The strength-duration curve may be measured directly by measuring the stimulation threshold at a plurality of pulse widths and then plotted, as shown in FIG. 5. The strength-duration curve may be measured manually by the physician (at implant), automatically by an external pacing systems analyzer (at implant), or automatically by the pacemaker.

Alternatively, the strength-duration curve may be expressed mathematically as:

$$V_{TH} = a \times PW^{-B} \tag{1}$$

where $V_{TH}$ is the stimulation (voltage) threshold in volts; PW is the pulse width in milliseconds;
"a" is a constant representing the voltage threshold measured at a desired pulse width (e.g., 1 msec) having units of volts/msec; and
"b" is a constant (approximately equal to 0.60).

Thus, in determining the strength-duration relationship for a given patient, all that is needed is to measure the stimulation threshold, $V_{TH}$, at a known pulse width (e.g., 1 millisecond) to estimate the constant "a", and then apply Eq. (1) to define the stimulation threshold at a variety of pulse widths and voltages. This is possible because the value "B" is substantially constant ($\cong 0.6$) and is relatively independent of the pacing lead.

In many instances, however, it is preferred to measure the strength-duration relationship at two points, thereby allowing estimation of both "a" and "B", and providing for a more precise estimation of the strength-duration relationship using Eq. (1).

Further, from Eq. (1), an expression for the Iso-Safety Factor Curve, (i.e., the family of stimulation amplitude/pulse widths needed to achieve a safety factor above the strength-duration curve) may be derived. That is, the stimulation (voltage) pulse amplitude, $V_{out}$, may be expressed as a function of stimulation threshold at a specified safety factor as:

$$V_{out} = SF \times V_{TH} \tag{2}$$
$$= SF \times a \times PW^{-B}$$

where SF is the desired safety factor.

Knowing the stimulation threshold and stimulation pulse amplitude as a function of pulse width, which can be derived using Eq. (2), it is then possible to determine the pacing current drain required of the pacemaker battery for each pulse amplitude and pulse width that could be used. Such determination is made using standard circuit modeling techniques, assuming periodic discharges from a discharge circuit made up of the output capacitor C charged to the pulse amplitude voltage, and discharged through a load R (see FIG. 2).

An expression for the pacing current drain derived using such standard circuit modeling techniques may be expressed as:

$$I_d = V_{out} \times C \times [1 - \exp^{-(PW/R \times C)}] \times (HR/60) \times CPF \quad (3)$$

where $I_d$ is the pacing current drain in microamps (ma);

C is the capacitance of the output capacitor in microfarads (μF);

HR is the stimulation rate of the pacemaker in stimulation pulses/minute;

PW is the pulse width in milliseconds (ms);

R is the pacing resistance; and

CPF is the charge pump factor.

The CPF is an integer, and for most pacemakers will either be 1, 2 or 3, meaning that the pacemaker voltage is multiplied by a factor of either 1, 2 or 3 in order to provide a sufficiently high voltage to generate a stimulation pulse having a pulse amplitude in excess of the battery voltage.

Substituting Eq. (2) into Eq. (3) provides an expression that defines pacing current drain as a function of the safety factor, "a", "B", pulse width (PW), charge pump factor (CPF), and pacing rate (HR). Such expression is:

$$I_d = SF \times a \times PW^{-B} \times C \times [1 - \exp^{-(PW/R \times C)}](HR/60) \times CPF \quad (4)$$

Figure 6:
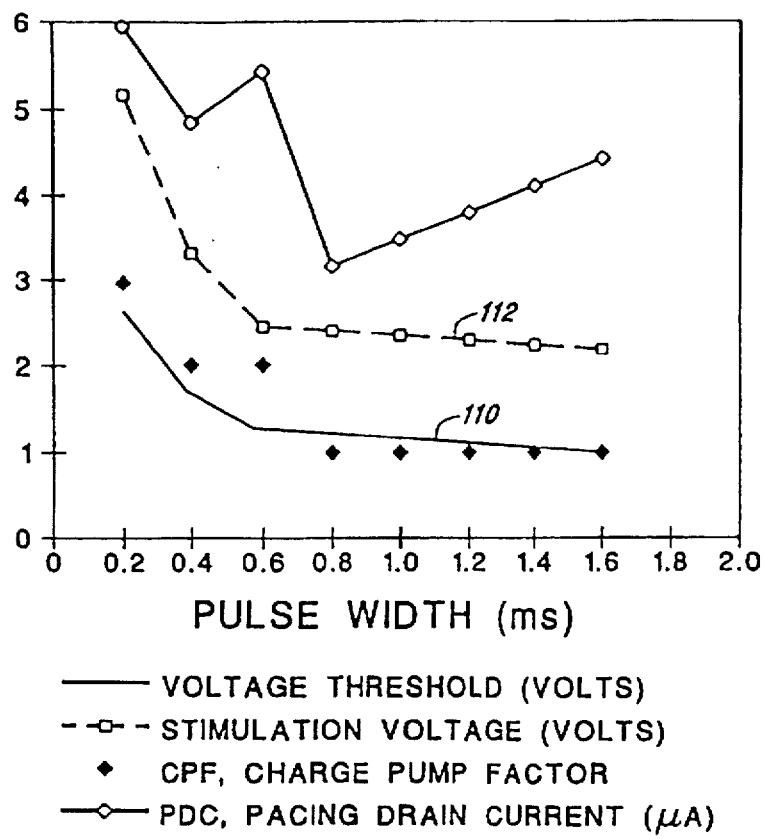
FIG. 6 is a graph as in FIG. 5, and further shows the current requirements from the pacemaker battery while stimulating at the various voltages shown on the stimulation voltage curve, and the charge pump multiplication factor used by the pacemaker in order to deliver a pulse having a voltage amplitude greater than the battery voltage.

As shown in FIG. 6, the pacing current drain, $I_d$, and the charge pump factor, CPF, can also be plotted with the strength-duration and Iso-Safety Factor curves. FIG. 6 clearly indicates that among the various possible pulse widths and pulse amplitudes that may be used to provide a safety factor of two, the minimal pacing current drain occurs at a pulse width of about 0.8 ms and a pulse amplitude of about 2.5 volts. Hence, given a choice of the various pulse widths and pulse amplitudes available along the specified Iso-Safety Factor Curve 112, it is possible (using Eq. 4) to determine an optimal pulse width and pulse amplitude that provide the lowest pacing current drain.

Thus, in accordance with the present invention, a series of stimulation pulses, of varying stimulation efficacy (i.e., varying energy) are defined so that each is formed from an optimal pulse width and pulse amplitude combination that minimizes the current drain while maximizing the safety factor. Selected ones of such series of pulses are then used by the pacemaker during its operation. Such process is broadly illustrated in the flow chart of FIG. 8.

Figure 8:
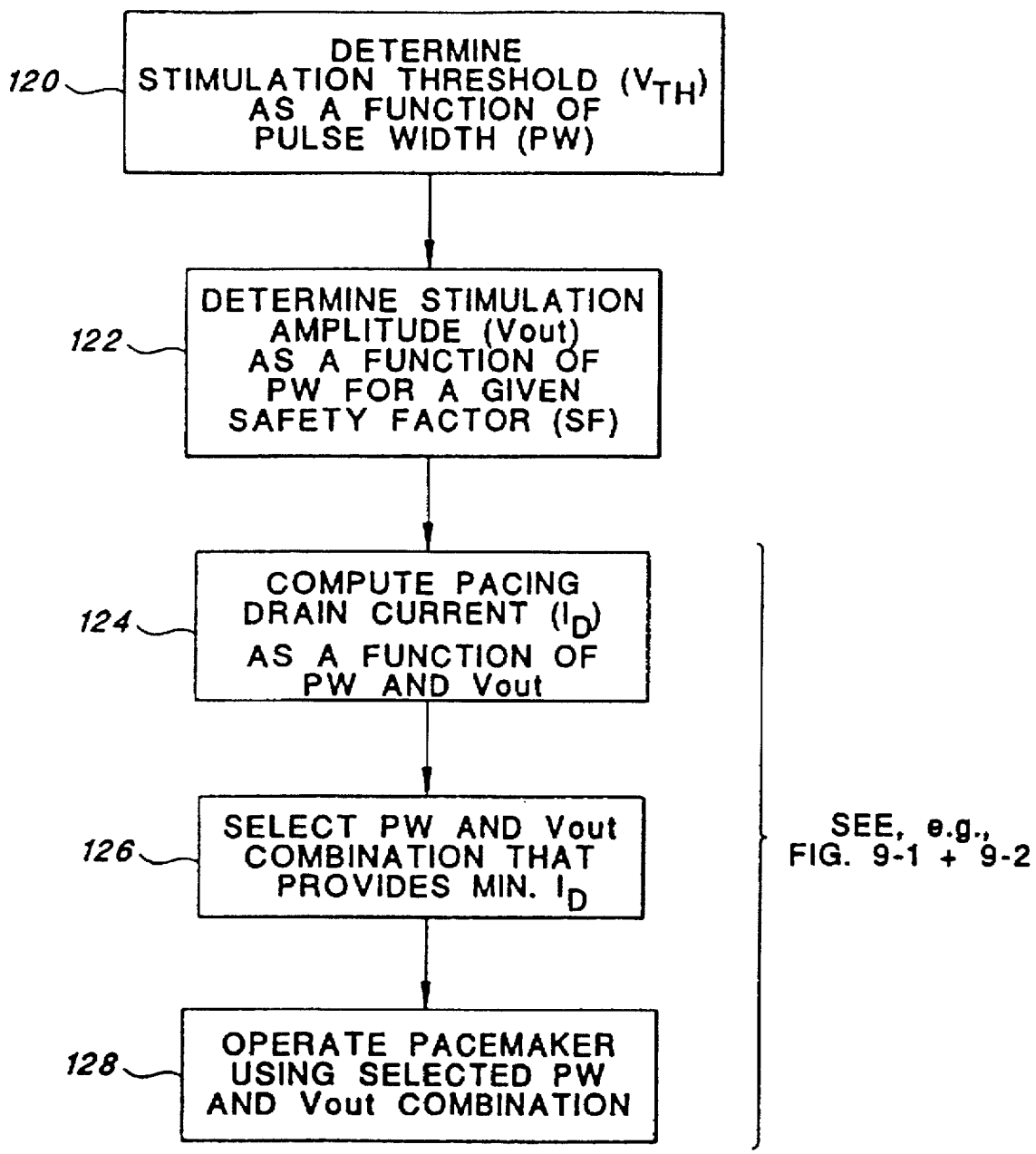
FIG. 8 is a flow chart that provides an overview of the method used by the present invention to automatically determine the optimal pacing energy, where "optimal" means a pacing energy designed to assure a desired safety factor while minimizing battery current drain.

A flow diagram of one embodiment of the present invention is shown in FIG. 8. That is, a first step in determining an optimal combination of pulse amplitude/pulse width (depicted in the block 120) involves determining the stimulation threshold as a function of pulse width. Such determination can be made through direct measurements, or by making enough measurements to determine the parameters "a" and "B" in Eq. (1) above, and thereafter using Eq. (1) to define the stimulation threshold.

Next, the stimulation amplitude, $V_{out}$, needed to provide a desired safety factor is determined (block 122) as a function of pulse width. Such determination is typically made by simply multiplying the stimulation threshold values (determined in block 120) by the safety factor. Alternatively, Eq. (2) may be used to define $V_{out}$.

Once $V_{out}$ as a function of pulse width is known, then the pacing current drain ($I_d$) is determined (block 124) for various values of $V_{out}$ and pulse width (PW), e.g., by computing the $I_d$ using Eq. (3) and/or standard circuit modeling techniques. With the pacing current drain known as a function of $V_{out}$ and PW, those combinations of PW and $V_{out}$ that provide minimum pacing current drain at a defined safety factor are selected as the optimal operating points of the pacemaker (block 126). Then, such operating points are programmed either by the external programmer 24 (FIG. 1) or automatically programmed by the pacemaker (block 128) as the desired operating points, thereby providing optimal stimulation, i.e., stimulation at an acceptable safety factor and at minimal battery drain current.

Figure 9A:
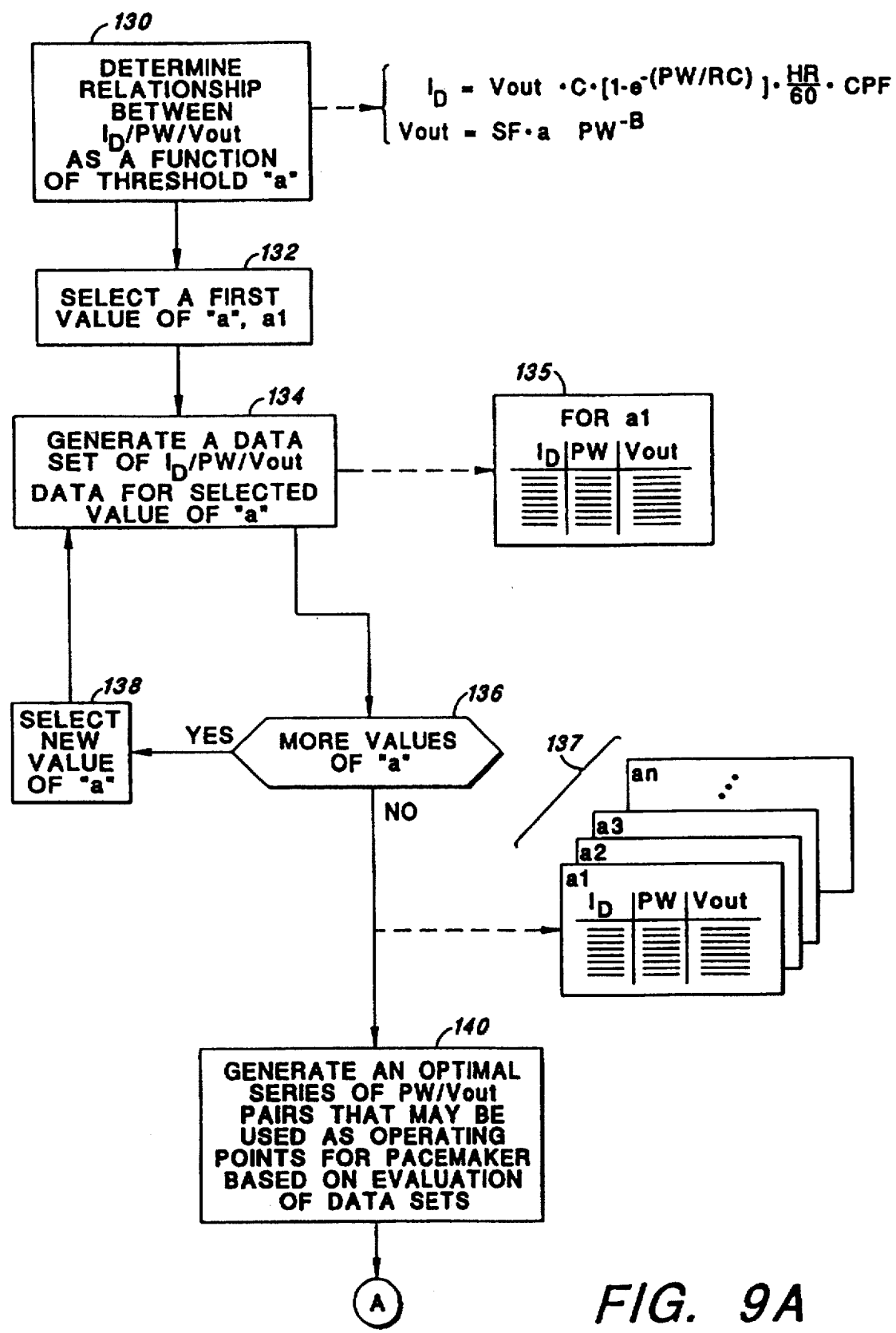
FIGS. 9A and 9B show a flow chart that details one technique that may be used in practicing the invention to arrive at "optimal" pacing energies.
Figure 9B:
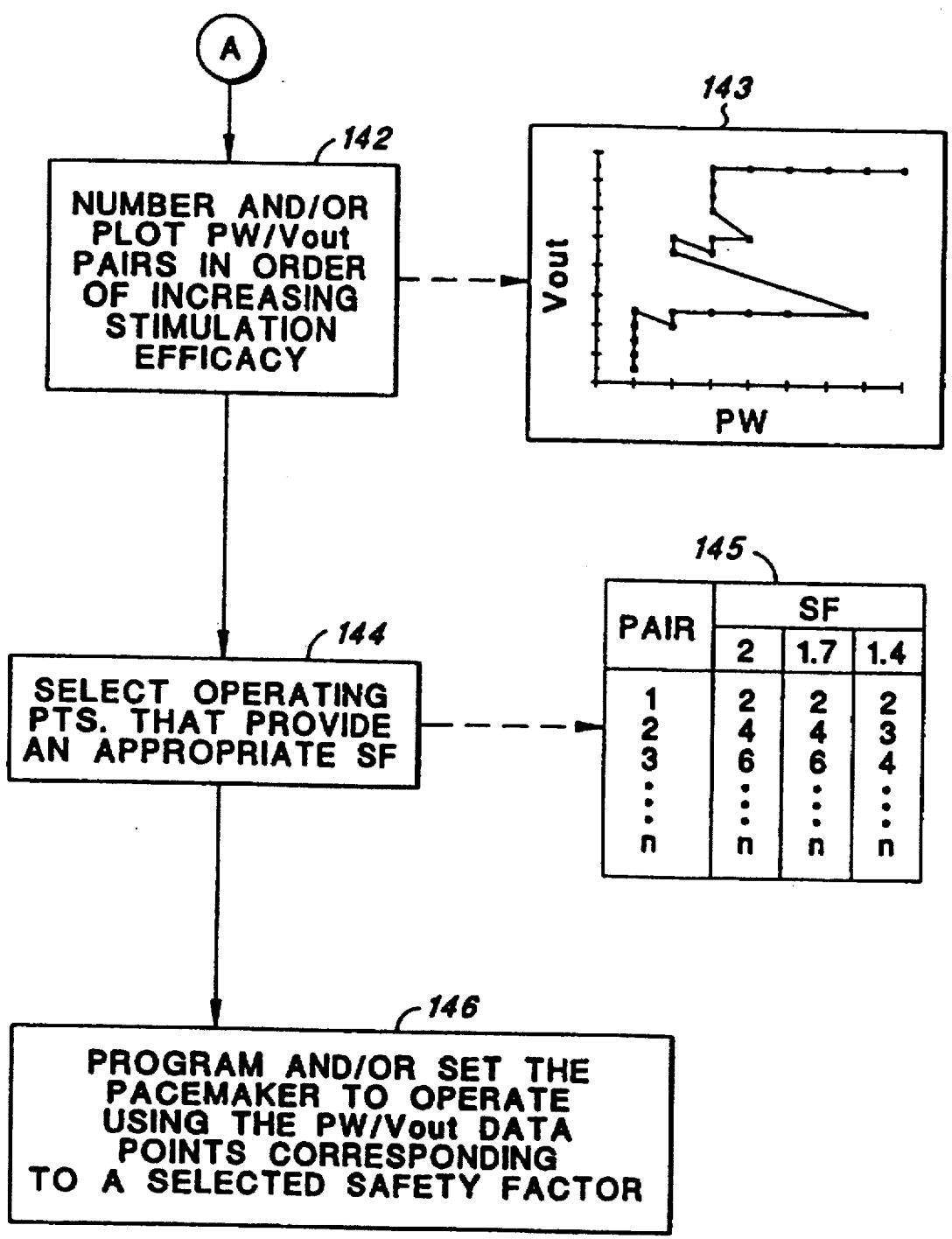

A preferred technique for carrying out the process depicted in blocks 124, 126 and 128 of FIG. 8 is further detailed in the flow chart of FIGS. 9A and 9B. (It is noted that FIGS. 9A and 9B show a single method, with the flow chart continuing from FIG. 9A to FIG. 9B.)

Starting with FIG. 9A, a first step of the method is to determine the relationship between the pacing current drain, pulse width and $V_{out}$ (block 130), e.g., using Eqs. (2), (3) and/or (4).

Next, a first value of the threshold constant "a" is selected (block 132). Such first value, referred to as "$a_1$", is then substituted into Eq. (4), with a fixed (known) safety factor, and a first data set is generated that relates $I_d$, PW and $V_{out}$ at such $a_1$ value (block 134). Such first data set may be arranged in or formatted as a table 135 having one column for the pacing current drain ($I_d$), once column for pulse width (PW), and one column for $V_{out}$.

This process is repeated for other stimulation threshold values of "a" (blocks 136 and 138). That is, other values of "a" (e.g., a second value $a_2$, a third value $a_3$, and so on, up to an nth value $a_n$) are substituted into Eq. (4), thereby generating second, third, . . . nth data sets. As a result, a multiplicity of data sets 137 are generated, each for a different threshold value "a", each relating the $I_d$, PW and $V_{out}$ at a particular threshold "a".

Using the information contained in the multiplicity of data sets 137, an optimal series of PW/$V_{out}$ pairs are generated that define the optimal operating points that may be used by the pacemaker (block 140). Each pair of the series is then numbered in order of increasing stimulation efficacy, i.e., increased power, and such points may be plotted (block 142). An example of such a series of pairs of operating points (pulse width versus voltage in available increments of 0.2 ms and 0.5 volts) is plotted in FIG. 7, which plot is symbolically reproduced in FIG. 9B as the plot 143.

Figure 7:
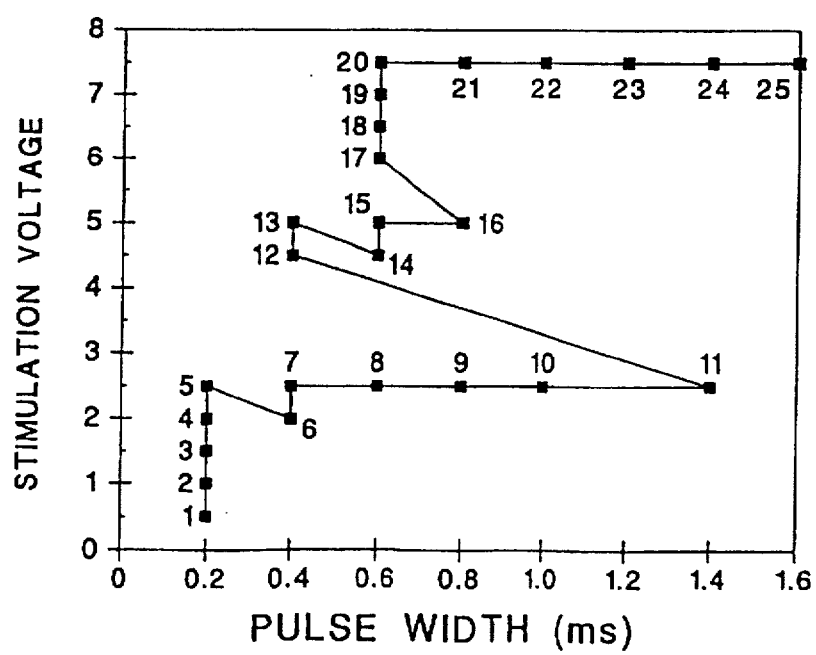
FIG. 7 is a graph that shows an optimal choice of pulse amplitude/width combinations, numbered in order of increasing stimulation efficacy, for use by a representative pacemaker so as to provide maximal safety factor while minimizing current drain.

As seen in FIG. 7, the first five operating points, points 1 through 5 of the optimal series, have the same pulse width, 0.2 ms, with increasing amplitude, 0.5 to 2.5 volts. Then, the sixth most effective operating point has its pulse width increased to 0.4 ms, and its amplitude decreased to 2.0 volts. Then, points 7-11 have increasing pulse widths, up to 1.4 ms for point 11, but maintain the amplitude at 2.5 volts. Point 12 reduces the pulse width back to 0.4 ms, but raises the amplitude to 4.5 volts; and point 13 keeps the pulse width at 0.4 ms and increases the amplitude to 5.0 volts. Point 14 reduces the amplitude to 4.5 volts, but increases the pulse width to 0.6 ms. Point 15 retains the pulse width of 0.6 ms and increases the amplitude to 5.0 volts. Point 16 retains the amplitude of 5.0 volts, but increases the pulse width to 0.8 ms. Points 17-20 all have a pulse width of 0.6 ms, with amplitudes increasing from 6.0 to 7.5 volts. Finally, points 21-25 retain the pulse amplitude of 7.5 volts, and increase the pulse width from 0.8 ms to 1.6 ms.

Referring to FIB. 9B, it is seen that once the series of optimal operating points are defined, selected ones of the points are chosen as the operating points for use by a given pacemaker in order to provide a desired safety factor (block 144). Not all of the operating points (e.g., not all of the 25 operating points shown in FIG. 7) are made available for use by a given pacemaker because not all of the points may satisfy the requirements for a given safety factor. Hence, depending upon the particular safety factor that is to be provided, a table of operating points is generated that provides the desired safety factor. Such table of operating points is symbolically represented in FIG. 9B as table 145, which table 145 contains actual operating points selected to provide the desired safety factor, as is shown and described below in connection with Table 2.

Once the operating points have been selected, such selected operating points are programmed into, or otherwise set within, the pacemaker so that the pacemaker always generates its stimulation pulses at the selected operating point(s) (block 146).

Table 1 shows the selected numbered operating points (col. 1) of FIG. 7 along with the equivalent stimulation voltage threshold (col. 4) at 1 ms pulse width located on the Iso-Safety Factor curve. Also included in Table 1 are the charge pump factor, CPF, (col. 5) and the equivalent pacing current drain, Id, (col. 6) required from the battery in order to generate each pulse.

TABLE 1

Selected Optimal Pulse Width and Stimulation Voltage Characteristics.

| Pair No. | PW (ms) | $V_{out}$ (volts) | Equiv. Stim. voltage @ 1 ms PW | CPF | Current Drain, $I_d$ | Pacing Energy 500 W mJoules |
|---|---|---|---|---|---|---|
| 1 | 0.2 | 0.5 | 0.22 | 1 | 0.20 | 0.09 |
| 2 | 0.2 | 1.0 | 0.45 | 1 | 0.39 | 0.37 |
| 3 | 0.2 | 1.5 | 0.67 | 1 | 0.59 | 0.84 |
| 4 | 0.2 | 2.0 | 0.89 | 1 | 0.79 | 1.50 |
| 5 | 0.2 | 2.5 | 1.08 | 1 | 0.96 | 2.34 |
| 6 | 0.4 | 2.0 | 1.37 | 1 | 1.51 | 2.81 |
| 7 | 0.4 | 2.5 | 1.69 | 1 | 1.86 | 4.39 |
| 8 | 0.6 | 2.5 | 2.19 | 1 | 2.72 | 6.18 |
| 9 | 0.8 | 2.5 | 2.35 | 1 | 3.49 | 7.75 |
| 10 | 1.0 | 2.5 | 2.48 | 1 | 4.22 | 9.12 |
| 11 | 1.4 | 2.5 | 2.70 | 1 | 5.58 | 11.38 |
| 12 | 0.4 | 4.5 | 3.05 | 2 | 6.74 | 14.22 |
| 13 | 0.4 | 5.0 | 3.37 | 2 | 7.44 | 17.56 |
| 14 | 0.6 | 4.5 | 3.94 | 2 | 9.77 | 20.03 |
| 15 | 0.6 | 5.0 | 4.39 | 2 | 10.87 | 24.73 |
| 16 | 0.8 | 5.0 | 4.74 | 2 | 14.04 | 31.00 |
| 17 | 0.6 | 6.0 | 5.28 | 3 | 19.62 | 35.61 |
| 18 | 0.6 | 6.5 | 5.72 | 3 | 21.27 | 41.79 |
| 19 | 0.6 | 7.0 | 6.14 | 3 | 22.81 | 48.46 |
| 20 | 0.6 | 7.5 | 6.58 | 3 | 24.46 | 55.63 |
| 21 | 0.8 | 7.5 | 7.09 | 3 | 31.52 | 69.75 |
| 22 | 1.0 | 7.5 | 7.47 | 3 | 38.13 | 82.11 |
| 23 | 1.2 | 7.5 | 7.82 | 3 | 44.43 | 92.93 |
| 24 | 1.4 | 7.5 | 8.11 | 3 | 50.21 | 102.39 |
| 25 | 1.6 | 7.5 | 8.40 | 3 | 55.80 | 110.67 |

It is noted that in Table 1, pacing energy is calculated as:

$$\text{Pacing Energy} = \int V(t) \cdot I(t) dt \qquad (5)$$
$$= V^2 \times (C/2) \times [1 - e^{-2 \times PW/(R \times C)}]$$

where V equals the stimulation voltage,

R is the load by the tissue, approx. 500 Ω, and

C is the value of the output capacitor, or approx. 5 uF.

As has been previously stated, and as is particularly evident from Table 1, the optimal operating points are numbered in order of increasing pacing energy. Such ordering turns out to be the same as being numbered in order of increasing pacing current drain, or in order of increasing equivalent stimulation voltage at 1 ms PW based on the Iso-Safety Factor curve.

Table 2 illustrates how the points shown in FIG. 7 or Table 1 may be used to provide an appropriate safety factor. Stimulation threshold is first measured using each operating point, i.e., points 1 through 25. Next, a stimulating operating point is selected from the optimal series of operating points using a selected safety factor. Safety factors of 2, 3 or 4, based on energy are common. Or, if based on voltage, the factors are based on the square root of energy, e.g., 1.414., 1.723, or 2, respectively.

TABLE 2

Output Level Setting Based on Threshold and Programmed Safety Factor

| THRESHOLD Output Pair Number | 4 × Energy SF = 2 Output Pair Number | 3 × Energy SF = 1.732 Output Pair Number | 2 × Energy SF = 1.414 Output Pair Number |
|---|---|---|---|
| 1 | 2 | 2 | 2 |
| 2 | 4 | 4 | 3 |
| 3 | 6 | 6 | 4 |
| 4 | 8 | 7 | 6 |
| 5 | 10 | 9 | 7 |
| 6 | 11 | 10 | 8 |
| 7 | 13 | 12 | 10 |
| 8 | 15 | 14 | 11 |
| 9 | 16 | 15 | 12 |
| 10 | 17 | 16 | 13 |
| 11 | 19 | 17 | 15 |
| 12 | 20 | 18 | 16 |
| 13 | 21 | 20 | 17 |
| 14 | 22 | 21 | 18 |
| 15 | 24 | 22 | 19 |
| 16 | 25 | 23 | 21 |
| 17 | 25 | 25 | 22 |
| 18 | 25 | 25 | 23 |
| 19 | 25 | 25 | 24 |
| 20 | 25 | 25 | 25 |
| 21 | 25 | 25 | 25 |
| 22 | 25 | 25 | 25 |
| 23 | 25 | 25 | 25 |
| 24 | 25 | 25 | 25 |
| 25 | 25 | 25 | 25 |

Table 2 thus depicts a family of optimal pulse widths and pulse amplitudes (voltages) that may be used to maximize the safety factor in a given pacemaker design. Such optimal pulse values are based on a pacemaker design that uses charge pump factors of 1, 2 and 3, a battery voltage of approximately 2.5 volts, and adjustable pulse widths and amplitudes in increments of 0.2 ms and 0.5 v, respectively, using 25 operating points. It should be emphasized, however, that other pacing devices may also be designed using the same techniques described herein.

It is noted that most modern pacemaker designs provide autocapture and autothreshold features with the goal of assuring that capture always occurs with a small but adequate safety factor while minimizing the pacing current drain on the battery. Representative autocapture and autothreshold features are described in copending patent applications, Ser. No. 07/980,941 (filed Nov. 23, 1992) and Ser. No. 07/844,818 (filed Mar. 2,1992), assigned to the same assignee as the present application, which patent applications are incorporated herein by reference. The present invention advantageously provides the framework for selecting optimal pulse width and pulse amplitudes that will help achieve such goal.

By minimizing the pacing current drain, many advantages accrue. For example, the pacemaker may use a smaller battery, and thus the pacemaker itself may be smaller. Further, current may be diverted away from stimulation and used for other, higher-order processes, such as the operation of a microprocessor. Additionally, the lifetime of the battery, and hence the life of the pacemaker, may be increased.

While the invention herein disclosed has been described by means of specific embodiments and applications thereof, numerous modifications and variations could be made thereto by those skilled in thereto by the art without departing from the scope of the invention set forth in the claims.

What is claimed is:

1. An implantable pacemaker comprising:

a battery;

pulse generating means for selectively generating electrical stimulation pulses at appropriate times for the purpose of depolarizing cardiac tissue, the electrical stimulation pulses being formed from electrical energy derived from the battery;

means for detecting capture at a patient's stimulation threshold; and pulse setting means, wherein the pulse setting means comprises:

means for determining a plurality of stimulation thresholds at a plurality of pulse widths at which capture is detected corresponding to a strength-duration curve;

means for adding a desired safety factor to the strength-duration curve to produce a plurality of pulse amplitude/pulse width combinations that would ensure capture at the desired safety factor;

means for determining a pacing current drain for each of the plurality of pulse amplitude/pulse width combinations that would ensure capture at the desired safety factor; and means for selecting an optimal pulse amplitude/pulse width combination corresponding to a pulse amplitude/pulse width combination which ensures capture at the desired safety factor with the lowest pacing current drain.

2. The implantable pacemaker, as set forth in claim 1, wherein the pulse setting means further comprises:

means, responsive to the capture detecting means, for determining a new stimulation threshold and for triggering a new optimal pulse amplitude/pulse width combination to be selected whenever capture is lost.

3. The implantable pacemaker, as set forth in claim 1, wherein the pulse setting means further comprises:

means for determining an optimal pulse amplitude/pulse width combination for each of a series of increasing strength-duration curves; and means for determining a sequence of optimal pulse amplitude/pulse width combinations based on the series of increasing strength-duration curves and having increased efficacy; and means for storing the sequence of optimal pulse amplitude/pulse width combinations so that if the stimulation threshold increases, then the next highest pulse in the sequence will be used as the optimal pulse amplitude/pulse width combination.

4. The implantable pacemaker, as set forth in claim 3, wherein the storing means comprises:

means for storing the sequence of optimal pulse amplitude/pulse width combinations as a plurality of energy data words, each energy data word including a pulse amplitude portion and a pulse width portion that define in combination an electrical stimulation pulse having a different stimulation efficacy, each energy word defining one of the plurality of pulse amplitude/pulse width combinations having increasing stimulation energy with the lowest overall pacing current drain.

5. The implantable pacemaker, as set forth in claim 4, further comprising:

a telemetry means, coupled to the pulse setting means, for establishing a telemetry link with an external programming unit, and for communicating the plurality of energy data words from the external programmer unit through the telemetry link to the memory means.

6. An implantable pacemaker comprising:

a battery;

automatic capture detection means, powered by the battery, for detecting capture and for measuring stimulation threshold whenever capture is lost;

stimulation means, powered by the battery, for generating electrical stimulation pulses of a prescribed pulse amplitude and width to cardiac tissue, the stimulation pulses being generated from electrical energy stored in the battery; and control means, powered by the battery, for defining a series of optimal pulse amplitude/pulse width combinations corresponding to a plurality of stimulation thresholds, wherein each of the pulse amplitude/pulse width combinations is calculated to minimize current drain on the battery as a function of a prescribed safety factor above a respective stimulation threshold; and selecting means, powered by the battery, for automatically selecting one of the series of optimal pulse amplitude/pulse combinations based on the measured stimulation threshold.

7. The implantable pacemaker, as set forth in claim 6, wherein:

the automatic capture detection means includes means for periodically measuring stimulation threshold; and the selecting means includes means for automatically selecting a new one of the series of optimal pulse amplitude/pulse width combinations whenever the measured stimulation threshold changes.

8. The implantable pacemaker, as set forth in claim 6, wherein the control means comprises:

memory means for storing a plurality of data words, a first data word defining a first pulse amplitude/width combination that maintains the prescribed safety factor at a first pacing energy and minimal current drain, a second data word defining a second pulse amplitude/width combination that maintains the prescribed safety factor at a second pacing energy and minimal current drain, the second pacing energy being greater than the first pacing energy; and so on, with an nth data word defining an nth pulse amplitude/width combination that maintains the prescribed safety factor at an nth pacing energy and minimal drain current, the nth pacing energy being greater than an (n−1)th pacing energy;

whereby an ordered set of n data words is stored in the memory means that defines a series of n stimulation pulses of increasing stimulation efficacy, each stimulation pulse having an amplitude and width combination that maintains the prescribed safety factor, yet minimizes current drain on the pacemaker battery.

9. The implantable pacemaker, as set forth in claim 8, further comprising:

a telemetry means, coupled to the control means, for establishing a communication link with an external programmer unit, the n data words being communicable through the telemetry link for storage within the memory circuit from the external programmer unit.

10. The implantable pacemaker, as set forth in claim 8, wherein the control means comprises:

means for adaptively and automatically adjusting which one of the n data words is selected to define the prescribed pulse amplitude and width of the electrical stimulation pulse generated by the stimulation means as a function of stimulation threshold.

11. An implantable pacemaker comprising:

a battery;

sensing means, powered by the battery, for sensing a cardiac rhythm;

control means, powered by the battery, for analyzing the sensed cardiac rhythm to determine if it is an acceptable rhythm as defined by a set of pre-defined parameters;

stimulation means, powered by the battery and controlled by the control means, for generating electrical stimulation pulses of a prescribed pulse amplitude and width that are generated and delivered to cardiac tissue at appropriate times so as to maintain the acceptable rhythm defined by the set of pre-defined parameters, the stimulation pulses being generated from electrical energy stored in the battery; and pulse forming means for defining an optimal pulse amplitude/pulse width combination as a pulse amplitude/pulse width combination that maintains a minimal current drain on the battery, as a function of a first prescribed safety factor when the rhythm is acceptable and as a function of a second prescribed safety factor when the rhythm is not acceptable.

12. The implantable pacemaker, as set forth in claim 11, wherein the pulse forming means comprises:

memory means for storing a plurality of data words, the plurality of data words defining a plurality of pulse amplitude/pulse width combinations, corresponding to a plurality of stimulation thresholds, that maintains the first and second prescribed safety factors with minimal current drain;

whereby a first and a second sequence of data words is stored in the memory means that defines a series of optimal pulse amplitude/pulse width combinations of increasing stimulation efficacy with the first and second prescribed safety factors, respectively, yet minimizes current drain on the pacemaker battery.

13. An implantable pacemaker that includes:

a battery;

means for detecting stimulation threshold;

pulse generating means, powered by the battery, for selectively generating electrical stimulation pulses, the electrical stimulation pulses having a pulse amplitude and pulse width that is defined by one of a plurality of operating points, each operating point being defined by a specific stimulation pulse amplitude and a specific stimulation pulse width, which pulse amplitude and pulse width have been calculated to provide a minimal pacing current drain on the battery as a function of a desired safety factor above the stimulation threshold.

14. The implantable pacemaker, as set forth in claim 13, further comprising:

control means for controlling the pulse generating means;

a telemetry means, coupled to the control means, for establishing a telemetry link with an external programmer, a set of command signals being transferable through the telemetry link from the external programmer to the control means, a single command signal within the set of command signals specifying an operating point at which the electrical stimulation pulses are to be generated whereby both a stimulation pulse width and stimulation pulse amplitude are programmed by transferring the single command signal through the telemetry link, and further whereby the stimulation pulse width and stimulation pulse amplitude thus programmed achieve a desired safety factor while maintaining a minimal drain current.

15. A pacing system for stimulating cardiac tissue with electrical stimulation pulses, the stimulation pulses having a pulse amplitude and width that assures that a given stimulation pulse, when delivered to the cardiac tissue, is above a stimulation threshold by a prescribed safety factor, the system comprising:

(1) an implantable pacemaker including:

(a) a battery, (b) control means, powered by the battery, for determining capture threshold, and (c) stimulation means, controlled by the control means, for generating electrical stimulation pulses of a prescribed pulse width and amplitude, and for delivering the electrical stimulation pulses to the cardiac tissue at appropriate times, the stimulation pulses being generated from electrical energy stored in the battery; and (2) an external programmer including:

(a) means for selectively establishing a communication link with the implantable pacemaker, (b) means for defining, through the communication link, the prescribed pulse amplitude and width of the stimulation pulses to be generated by the stimulation means of the implantable pacemaker, the prescribed pulse amplitude and pulse width being calculated, as a function of a prescribed safety factor, to draw minimal energy from the battery of the implantable pacemaker.

16. The pacing system, as set forth in claim 15, wherein the means for defining the prescribed pulse amplitude and width comprises:

a memory circuit wherein a series of stimulation pulse operating points of increasing stimulation efficacy are defined, each operating point defining a stimulation pulse of increasing stimulation energy that is realized by a specific stimulation pulse amplitude in combination with a specific stimulation pulse width that maintains the prescribed safety factor, and that draws minimal energy from the battery.

17. The pacing system, as set forth in claim 16, wherein the control means of the implantable pacemaker further comprises:

means for measuring a stimulation threshold as a function of a prescribed stimulation pulse width;

means for communicating the measured stimulation thresholds to the external programmer through the communication link; and wherein the external programmer includes processing means for processing the measured stimulation thresholds so as to generate the series of stimulation pulse operating points.

18. The pacing system, as set forth in claim 16, wherein the series of stimulation pulse operating points includes at least 20 points.

19. A method of operating an implantable pacemaker to use optimal stimulation pulse widths and stimulation pulse amplitudes as it performs its stimulation function, the optimal selection being made to minimize the pacemaker current drain while maximizing a safety factor of the pacemaker, the method comprising the steps of:

(a) determining a stimulation threshold for a particular patient as a function of stimulation pulse width;

(b) determining a stimulation pulse amplitude as a function of stimulation pulse width so as to achieve a given safety factor above the stimulation threshold;

(c) computing a pacing current drain as a function of the stimulation pulse widths and amplitudes determined in step (b);

(d) selecting a stimulation pulse amplitude and pulse width combination that provides a minimal pacing current drain as a function of pacing energy; and (e) programming the pacemaker to use the stimulation pulse amplitude and pulse width combination determined in step (d).

20. The method, as set forth in claim 19, wherein steps (c) and (d) include:

defining a relationship between pacing current drain, stimulation threshold, pulse amplitude, pulse width and safety factor;

selecting a desired safety factor;

generating a plurality of data sets for the pacing current drain, pulse amplitude, pulse width and safety factor for a plurality of stimulation thresholds;

evaluating the plurality of data sets to determine optimal pulse width and pulse amplitude pairs that may be used as operating points for the pacemaker at each stimulation threshold, the optimal pulse width and pulse amplitude pairs being defined as the pair which achieves the desired safety factor with the lowest current drain;

determining a sequence for the optimal pulse width and pulse amplitude pairs in order of increasing stimulation efficacy;

measuring a given patient's stimulation threshold; and selecting operating points for the pacemaker from the sequence of pulse width and pulse amplitude pairs so as to provide a selected safety factor above the patient's stimulation threshold with the lowest current drain.

21. The method, as set forth in claim 20, wherein the pacemaker includes an output capacitor that stores the energy of the stimulation pulse, which stimulation pulse is delivered to a known pacing resistance, and wherein:

the step of defining the relationship between pacing current drain ($I_d$), stimulation threshold ($V_{TH}$), pulse amplitude ($V_{out}$), pulse width (PW), and safety factor (SF) comprises defining:

$I_d = V_{out} \times C \times [1-e^{-(PW/RC)}] \times (HR/60) \times CPF$; and $V_{TH} = a \times PW^{-B}$ $V_{out} = SF \times a \times PW^{-B}$ where $V_{out}$ is the pulse amplitude in volts, PW is the pulse width in milliseconds, R is the pacing resistance, C is the capacitance value of the output capacitor in microfarads, HR is the stimulation rate provided by the pacemaker in stimulations/minute, and CPF is a charge-pump-factor that defines how many times the battery voltage of the pacemaker is stepped-up or multiplied in order to place a sufficient voltage on the output capacitor to achieve a specified pulse amplitude, "a" and "B" are constants for a given stimulation threshold.

22. The method, as set forth in claim 21, wherein the constant "a" can be estimated by measuring the stimulation threshold of a patient at approximately 1 msec.

23. The method, as set forth in claim 22, wherein the constant "B" is approximately 0.60.

24. The method, as set forth in claim 22, wherein the step of generating a plurality of data sets comprises the step of:

determining the plurality of stimulation thresholds by varying the constant "a" to produce a plurality of strength-duration curves.

25. A method of operating an implantable pacemaker to use optimal stimulation pulse widths and stimulation pulse amplitudes as it performs its stimulation function, the optimal selection being made to minimize the pacemaker current drain while maximizing a safety factor of the pacemaker, the method comprising the steps of:

(a) determining a strength-duration curve for a particular patient;

(b) determining an Iso-Safety Factor curve corresponding to a plurality of stimulation pulse amplitude/pulse width combinations which achieve a given safety factor above the strength-duration curve;

(c) computing a pacing current drain as a function of the stimulation pulse widths and amplitudes determined in step (b);

(d) selecting an optimal stimulation pulse amplitude and pulse width combination that provides a minimal pacing current drain as a function of pacing energy; and (e) programming the pacemaker to use the stimulation pulse amplitude and pulse width combination determined in step (d).

26. A method of operating an implantable pacemaker, having a discharge circuit, to use optimal stimulation pulse widths and stimulation pulse amplitudes as it performs its stimulation function, the optimal selection being made to minimize the pacemaker current drain while maximizing a safety factor of the pacemaker, the method comprising the steps of:

(a) determining a strength-duration curve for a particular patient;

(b) determining an Iso-Safety Factor curve corresponding to a plurality of stimulation pulse amplitude/pulse width combinations which achieve a given safety factor above the strength-duration curve;

(c) computing a pacing current drain as a function of the discharge circuit and stimulation pulse widths and amplitudes determined in step (b);

(d) selecting an optimal stimulation pulse amplitude and pulse width combination that provides a minimal pacing current drain; and (e) programming the pacemaker to use the stimulation pulse amplitude and pulse width combination determined in step (d).

27. The implantable pacemaker of claim 26, wherein the discharge circuit comprises a charge pump, output capacitor and pacing load and wherein computing the pacing current drain as a function of the discharge circuit considers the charge pump factor; capacitance of the output capacitor; and pacing load.

28. An implantable pacemaker comprising:

a battery;

a discharge circuit, comprising a charge pump, output capacitor and pacing load;

pulse generating means for selectively generating electrical stimulation pulses at appropriate times for the purpose of depolarizing cardiac tissue, the electrical stimulation pulses being formed from electrical energy derived from the battery;

means for detecting capture at a patient's stimulation threshold; and pulse setting means, wherein the pulse setting means comprises:

means for determining a plurality of stimulation thresholds at a plurality of pulse widths at which capture is detected corresponding to a strength-duration curve;

means for adding a desired safety factor to the strength-duration curve to produce a plurality of pulse amplitude/pulse width combinations that would ensure capture at the desired safety factor;

means for determining a pacing current drain, as a function of the discharge circuit, for each of the plurality of pulse amplitude/pulse width combinations that would ensure capture at the desired safety factor, wherein said means includes consideration of the charge pump factor, capacitance of the output capacitor and pacing load; and means for selecting an optimal pulse amplitude/pulse width combination corresponding to a pulse amplitude/pulse width combination which ensures capture at the desired safety factor with the lowest pacing current drain.

29. An implantable pacemaker that includes:

a battery;

means for detecting stimulation threshold;

means for determining a stimulation efficacy as a function of the stimulation threshold and a desired safety factor; and pulse generating means, powered by the battery, for selectively generating electrical stimulation pulses, the electrical stimulation pulses having a pulse amplitude and pulse width that is defined by one of a plurality of operating points, each operating point providing a different stimulation efficacy and being defined by a specific stimulation pulse amplitude and pulse width combination that minimizes current drain for that stimulation efficacy.

30. The implantable pacemaker, as set forth in claim 29, further comprising:

control means for controlling the pulse generating means;

a telemetry means, coupled to the control means, for establishing a telemetry link with an external programmer, a set of command signals being transferable through the telemetry link from the external programmer to the control means, a single command signal within the set of command signals specifying an operating point at which the electrical stimulation pulses are to be generated, whereby both a stimulation pulse width and stimulation pulse amplitude are programmed by transferring the single command signal through the telemetry link, and further whereby the stimulation pulse width and stimulation pulse amplitude thus programmed achieve a desired safety factor while maintaining a minimal drain current.

31. A pacing system for stimulating cardiac tissue with electrical stimulation pulses, the stimulation pulses having a pulse amplitude and width that assures that a given stimulation pulse, when delivered to the cardiac tissue, is above a stimulation threshold by a prescribed safety factor, the system comprising:

(1) an implantable pacemaker including:
   (a) a battery,
   (b) control means, powered by the battery, for determining capture threshold, and
   (c) stimulation means, controlled by the control means, for generating electrical stimulation pulses of a prescribed pulse width and amplitude, and for delivering the electrical stimulation pulses to the cardiac tissue at appropriate times, the stimulation pulses being generated from electrical energy stored in the battery; and (2) an external programmer including:
   (a) means for selectively establishing a communication link with the implantable pacemaker,
   (b) means for defining, through the communication link, a series of stimulation pulse operating points of increasing stimulation efficacy, each operating point defining a stimulation pulse of increasing stimulation energy that is realized by a specific stimulation pulse amplitude in combination with a specific stimulation pulse width that draws minimal energy from the battery as a function of the prescribed safety factor.

32. The pacing system, as set forth in claim 31, wherein the control means of the implantable pacemaker further comprises:

means for measuring a stimulation threshold as a function of a prescribed stimulation pulse width;

means for communicating the measured stimulation thresholds to the external programmer through the communication link; and wherein the external programmer includes processing means for processing the measured stimulation thresholds so as to generate the series of stimulation pulse operating points.

33. The pacing system, as set forth in claim 31, wherein the series of stimulation pulse operating points includes at least 20 points.

* * * * *